(12) United States Patent
Krämer et al.

(10) Patent No.: US 7,304,089 B2
(45) Date of Patent: Dec. 4, 2007

(54) PREPARATION FOR IMPROVED DIETARY UTILISATION

(75) Inventors: Klaus Krämer, Landau (DE); Oliver Hasselwander, Landau (DE); Uwe Oberfrank, Römerberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 569 days.

(21) Appl. No.: 10/250,567

(22) PCT Filed: Jan. 16, 2002

(86) PCT No.: PCT/EP02/00370

§ 371 (c)(1),
(2), (4) Date: Jul. 3, 2003

(87) PCT Pub. No.: WO02/056708

PCT Pub. Date: Jul. 25, 2002

(65) Prior Publication Data

US 2004/0047894 A1 Mar. 11, 2004

(30) Foreign Application Priority Data

Jan. 17, 2001 (DE) ................ 101 02 050

(51) Int. Cl.
*A61K 31/385* (2006.01)
*A61K 31/22* (2006.01)
*A61K 31/205* (2006.01)
*A61K 31/20* (2006.01)
*A23D 9/007* (2006.01)

(52) U.S. Cl. .............. 514/440; 514/549; 514/556; 514/560; 426/601

(58) Field of Classification Search .............. None
See application file for complete search history.

(56) References Cited

U.S. PATENT DOCUMENTS

| | | | |
|---|---|---|---|
| 3,162,658 A | 12/1964 | Baltes et al. | |
| 3,356,694 A | 12/1967 | Lunn | |
| 3,356,699 A | 12/1967 | Bagby et al. | |
| 5,376,374 A * | 12/1994 | Zelaya | 424/726 |
| 5,665,386 A * | 9/1997 | Benet et al. | 424/451 |
| 6,106,847 A * | 8/2000 | Ferrero et al. | 424/401 |
| 6,197,305 B1 * | 3/2001 | Friedman et al. | 424/737 |
| 6,444,238 B1 * | 9/2002 | Weise | 424/736 |
| 2002/0045232 A1 * | 4/2002 | Qiu | 435/190 |

FOREIGN PATENT DOCUMENTS

| | | |
|---|---|---|
| DE | 1 141 690 | 5/1961 |
| DE | 1 156 788 | 11/1963 |
| DE | 1 156 789 | 11/1963 |
| EP | 839 897 | 5/1998 |
| EP | 1 175 901 | 1/2002 |
| GB | 921688 | 3/1963 |
| GB | 925148 | 5/1963 |
| WO | 94/16690 | 8/1994 |
| WO | 96/06605 | 3/1996 |
| WO | 97/32008 | 9/1997 |
| WO | 97/46118 | 12/1997 |
| WO | 97/46230 | 12/1997 |
| WO | 99/29317 | 6/1999 |
| WO | 00/11167 | 3/2000 |

OTHER PUBLICATIONS

Cecil Textbook of Medicine, 21st Edition, vol. 1, published in 2000 by W.B. Saunders Company (PA), pp. 1060-1074.*
"Calendula", by author Bruce Burnett, CH, from http://www.alive.com/224a1a2.php?subject_bread_cramb=814, Source: Alive #213, Jul. 2000, downloaded on Mar. 17, 2006.*
"Homeopathic Calendula" by author Diane Fuller, DHom, from http://www.alive.com/589a2a2.php?subject_bread_cramb=814, Source: Alive #224, Jun. 2001, downloaded on Mar. 17, 2006.*
The Merck Index, 11th edition, published in 1989 by Merck & Co., Inc., (NJ), p. 1081, cit. No. 6796 "Olive oil".*
J.of Food Composition and Analysis 5, 1992: 185-197,Chin et al.
Carcinogenesis, Banni et al., vol. 20, 1999: 1019-1024.
Thompson, Cancer Research, vol. 57, 1997:5067-5072.
Chemistry of Natural Compounds, vol. 34,No. 3, 1998, Ul'chenko et al.
J.Chem.Soc., No. 15, 1984, Crombie et al.
J.Soc.Perkin Trans, 1985, Crombie et al.
Lipids, vol. 32,No. 8(1997), Park et al.
J.J.American College of Nutrition, (2000)19, 111S-118S, MacDonald.
XP-2207591, Yurawecz et al., (JAOCS, vol. 70, No. 1, Nov. 1993).

(Continued)

*Primary Examiner*—Raymond J. Henley, III
(74) *Attorney, Agent, or Firm*—Novak Druce & Quigg, LLP

(57) ABSTRACT

Food, feed or drug preparations are described that contain conjugated trans/cis-octadecatrienoic acid, and processes are described for their production. Inventive preparations preferably comprise calendic acid. The invention also relates to the use of the preparations to reduce food intake in humans and animals and to improve food utilization.

9 Claims, 6 Drawing Sheets

OTHER PUBLICATIONS

XP 002063858, Nugteren et al. (Mar. 1987, vol. 33, No. 3).
XP 000973303, Takagi et al., date not available.
Lipids, vol. 1(1966)325-327, Earle et al.
Lipids, vol. 17, No. 10(1982) 716-722, Takagi et al.
XP 000973904, Dhar et al., 109-114, Lipids, vol. 34,No. 2(1999).
XP 002162410, Dhar et al., Annals of Nutr.&Metab., Sep.-Oct. 1998.
Patent Abst.of Japan,(2000)336 029.

* cited by examiner

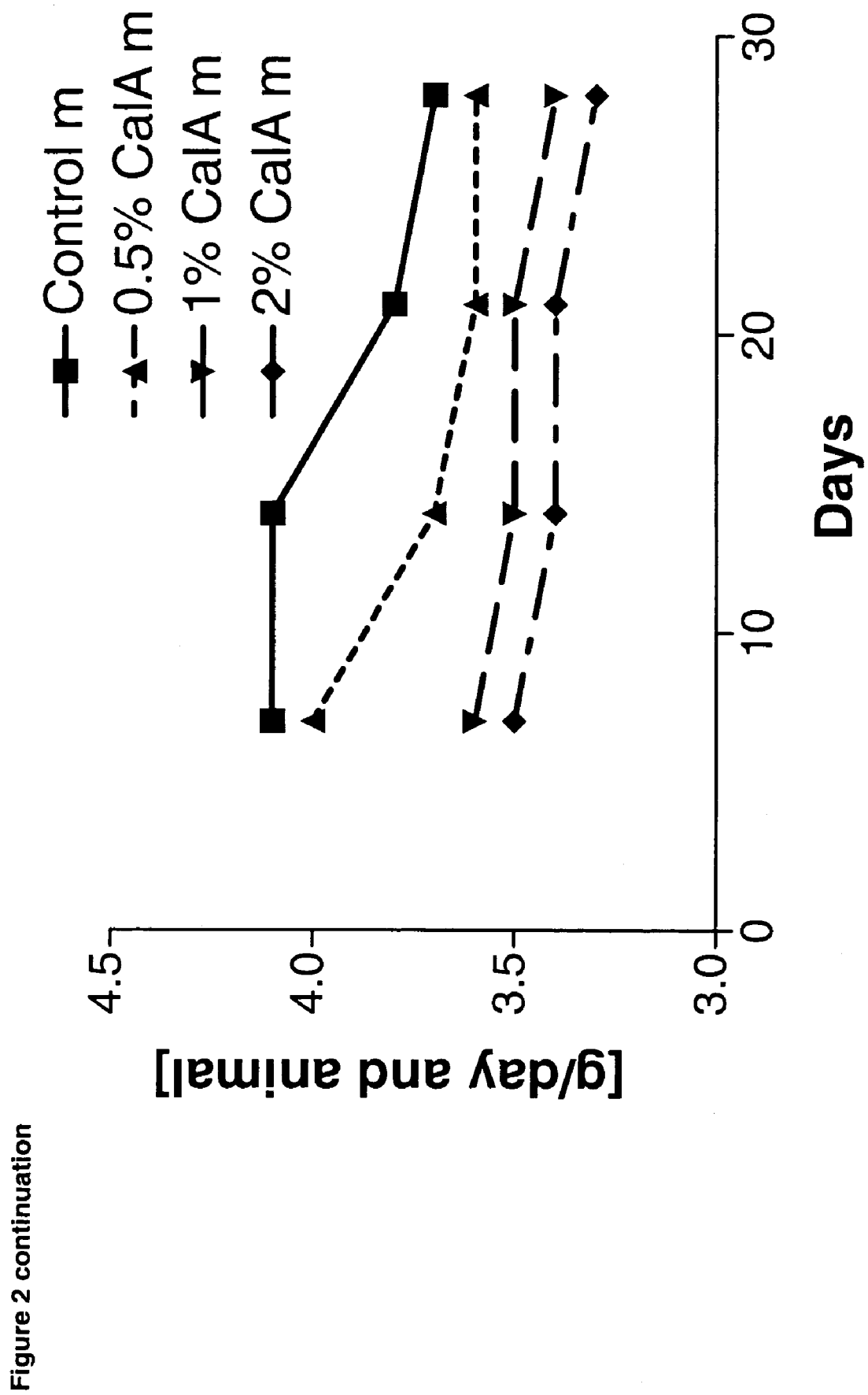
Figure 2 continuation

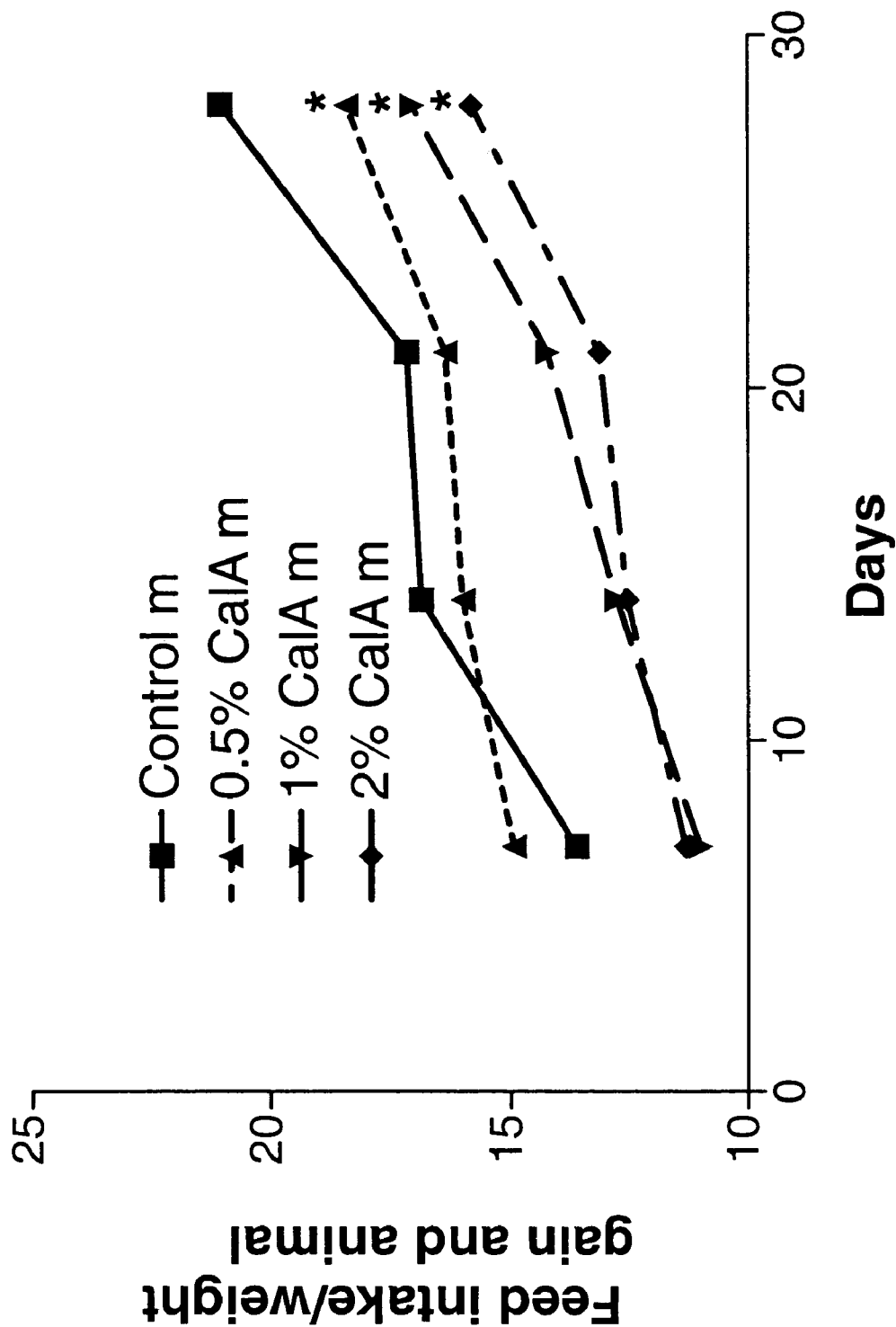
Figure 3 continuation

PREPARATION FOR IMPROVED DIETARY UTILISATION

The present invention relates to food, nutrient or drug preparations that comprise conjugated trans/cis-octadecatrienoic acid and to processes for their production. Inventive preparations preferably comprise calendic acid. The invention also relates to the use of the preparations for reducing food intake in humans and animals and for improved food utilization in humans and animals, changing the body composition, processes for reducing the nutrient intake and a kit that comprises the inventive preparation.

Fatty acids and triglycerides have a multiplicity of applications in the food industry, animal nutrition, cosmetics and the pharmaceutical sector. Depending on whether they are free saturated or unsaturated fatty acids, or triglycerides having an elevated content of saturated or unsaturated fatty acids, they are suitable for the most varied applications. Thus, for example, a high content of lipids containing unsaturated fatty acids, and especially containing polyunsaturated fatty acids, are important for the nutrition of animals and humans, since these have, for example, a beneficial effect on the triglyceride level or cholesterol level in the blood and thus decrease the risk of heart disease. Unsaturated fatty acids are used in various dietetic foods or medicaments.

Particularly valuable and sought-after unsaturated fatty acids are the conjugated unsaturated fatty acids. Conjugated polyunsaturated fatty acids are somewhat rare, compared with other polyunsaturated fatty acids.

CLA is a collective term for positional and structural isomers of linoleic acid that are distinguished by a conjugated double bond system on carbon atom 8, 9, 10 or 11. Geometric isomers exist for each of these positional isomers, that is to say cis-cis, trans-cis, cis-trans, trans-trans. Especially C18:2 cis-9, trans-11 and C18:2 trans-10, cis-12 CLASs, which have the most biologically active isomers, are of particular interest, since they have proved in animal experiments that they prevent cancer, have anti-arteriosclerotic action and reduce the body fat content in humans and animals. Commercially, CLAs are now principally marketed as free fatty acids.

For humans, the most important natural sources of CLAs are primarily animal fats. Thus fats of ruminant animals, such as cattle (Chin, Journal of Food Composition and Analysis, 5, 1992: 185-197) and sheep, and also dairy products, have very high CLA concentrations. In cattle, contents of from 2.9 to 8.9 mg/g of fat are found. In contrast, vegetable oils, margarines and fats from non-ruminant animals have CLA concentrations of only from 0.6 to 0.9 mg/g of fat.

(II)

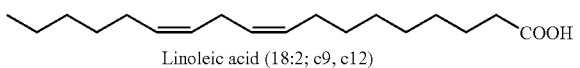

Linoleic acid (18:2; c9, c12)

(III)

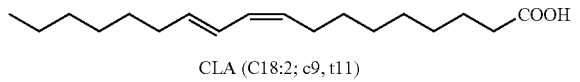

CLA (C18:2; c9, t11)

-continued (IV)

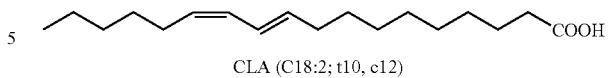

CLA (C18:2; t10, c12)

A number of beneficial effects have been found for CLA. Thus administering conjugated linoleic acid decreases body fat in humans and animals and increases feed conversion per kilogram of bodyweight in animals (WO 94/16690, WO 96/06605, WO 97/46230, WO 97/46118). Also, administering conjugated linoleic acid beneficially affects, for example, allergies (WO 97/32008), diabetes (WO 99/29317) or cancer (Banni, Carcinogenesis, Vol. 20, 1999: 1019-1024, Thompson, Cancer, Res., Vol. 57, 1997: 5067-5072). Polyunsaturated fatty acids are also added to baby food to "increase the nutritional value" and as essential building blocks which ensure growth and brain development.

CLA, as described above, has very extensive beneficial nutritional effects. However, CLA occurs in significant amounts naturally only in ruminants and their products, such as milk, cheese. There is therefore a great requirement for alternatives to CLA originating from these animal sources, in particular to ensure balanced and health nutrition in less developed regions, where the supply with these animal fats is inadequate or synthetic preparation is too expensive. However, the consumption of meat and milk products has also decreased in developed regions, in order to decrease the proportion of saturated fatty acids which are deemed to be unhealthy. However, this also means a decrease in the intake of "healthy" CLA.

It is an object of the present invention to provide an alternative preparation which has similar advantageous nutritional effects to a preparation comprising CLA.

We have found that this object is achieved by the embodiments underlying the present invention.

The present invention therefore relates to a food, food supplement, animal feed or drug preparation comprising conjugated trans/cis-octadecatrienoic acid.

The surprising finding underlying the present invention is that adding conjugated trans/cis-octadecatrienoic acid, in particular calendic acid, to the diet leads to a decreased dietary intake without a reduction in bodyweight being observed. That is to say the feed utilization is significantly improved when conjugated octadecatrienoic acid is added to the diet. The term "octadecatrienoic acid" or the term "calendic acid" comprises herein not only the free acid, but also the salts and esters and nontoxic derivatives. Preferably, the term comprises nontoxic salts or glycerides, in particular triglycerides, or ethyl esters or methyl esters as described below.

Surprisingly it has also been found that by adding a conjugated trans/cis octadecatrienoic acid, in particular calendic acid, a change in body composition can be observed. Thus it has been found that adding calendic acid leads to a reduction in the body fat content in the animal body.

The present invention thus additionally relates to a process for producing a food, food supplement, animal feed or drug preparation which comprises adding a conjugated trans/cis-octadecatrienoic acid to the preparation. Preferably, said trans/cis-octadecatrienoic acid has a t10, c12 configuration.

In a particularly preferred embodiment, said trans/cis-octadecatrienoic acid is therefore calendic acid. Calendic acid is a C18:3 fatty acid having a t8, t10, c12 configuration.

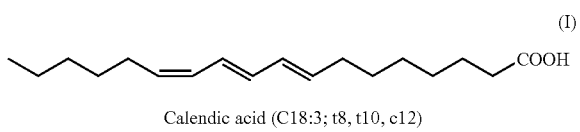

Calendic acid (C18:3; t8, t10, c12)

It is thus a conjugated trans/cis-octadecatrienoic acid. Calendic acid is the fatty acid responsible for the observed inventive reduction in dietary intake and improved feed utilization in mice when calendula oil is added to the feed, as shown by the comparative experiments in the examples using corn oil. Chemical preparation of calendic acid is described in U.S. Pat. No. 3,356,699. Calendic acid occurs naturally, for example, in *Calendula officinalis* (Earle et al., Lipids, 1, 1964: 325-327, Takagi et al., Lipids, 17, 1981: 716-723, Ul'chenko et al., Lipids of *Calendula officinalis*, Chemistry of Natural Compounds, 34, 1998: 272-274). Biochemical studies on the synthesis of calendic acid may be found in Crombie et al., J. Chem. Soc. Chem. Commun., 15, 1984: 953-955 and J. Chem. Soc. Perkin Trans., 1, 1985: 2425-2434.

Other conjugated trans/cis octadecatrienoic acids can be formed by chemically modifying linolenic-acid-containing oils, for example from linseed oil, soybean oil or hemp oil.

Inventive preparations are outstandingly suitable as food or feed additives, for example in diets or in the case of animal fattening. Thus calendic acid can be used in combination or else alone with reduced calorie intake for supporting a diet, for example for reducing bodyweight in humans, which advantageously also affects eating behavior. Improved utilization of the food consumed leads to reduction in nutrient consumption, which can be advantageous particularly in less developed areas having a food shortage, or in extreme situations (diseases, high-energy sport). Furthermore, it is advantageously possible to achieve a change in the body composition, particularly a reduction in the fat content of the body.

Inventive preparations can also be used economically and ecologically advantageously in animal nutrition, in particular for reducing the amount of feed or the fat content of animals. There is currently great interest in society in the fat content of the diet. Because of the suspected relationship between saturated fatty acids of meat and blood cholesterol content, attention is being paid to a low-fat diet. Therefore, there is great interest in methods for reducing the fat content of animals, such as, in particular, by the present invention.

In one embodiment, the conjugated trans/cis-octadecatrienoic acid or the calendic acid is present in the preparation as calendula oil.

"Calendula oil" is taken to mean a fatty acid mixture that contains calendic acid. Preferably, the content of calendic acid in calendula oil is approximately 30%, more preferably 50%, still more preferably 60%, 70%, 80% or 90%. Most preference is given to a content of 95% or more. For this, for example, the calendic acid content can be determined by gas chromatography after saponification of fatty acids and conversion of the fatty acids to methyl esters. In addition to calendic acid, the calendula oil can contain various other saturated or unsaturated fatty acids, for example linoleic acid, palmitic acid. In particular, depending on the production process, the content of the various fatty acids in calendula oil can vary. Each fatty acid pattern is covered by the inventive preparation, in particular fatty acid patterns which are formed in the production of oil from plant material, and has said calendula oil content. Preferably, the calendula oil has low variation of differing fatty acids and the number of different fatty acids in the calendula oil is small.

In a further embodiment, said preparation comprises other additives.

"Additives" are taken to mean other additions which are advantageous for nutrition or health, for example "nutrients", "dietary additives" or "active compounds". The preparation can comprise one or more additives for animal or human nutrition or treatment and can be diluted or mixed therewith. Additives can be administered together with, or separately from, the feed, food, food supplement or drug. A food, food supplement, animal feed or drug preparation does not contain any additives, or any amounts of additives, that can be considered as harmful for animal or human nutrition.

"Nutrients" are taken to mean those additives which are advantageous for the nutrition of humans or animals. Preferably, the inventive preparation therefore also comprises vitamins, for example vitamins A, B1, B2, B6, B12, C, D3 and/or E, folic acid, nicotinic acid, taurine, carboxylic acids, for example tricarboxylic acids, citrate, isocitrate, trans/cis-aconitate, and/or homocitrate, enzymes, for example phytases, carotenoids, minerals, for example P, Ca, Mg, Mn and/or Fe, proteins, carbohydrates, fats, amino acids and/or trace elements Sn. The preparation can also comprise pyruvic acid, L-carnitine, lipoic acid, coenzyme Q10, aminocarboxylic acids, for example creatine. "Active compounds" are taken to mean those substances which support the use of the inventive preparation as drug, or whose action serves for treating disorders, in particular treating cancer, diabetes, AIDS, allergies and cardiovascular disorders (see also below). Therefore, the inventive preparation can also include preservatives, antibiotics, antimicrobial additives, antioxidants, chelating agents, inert gases, physiologically harmless salts etc. Those skilled in the art know the additives which are to be added to the preparation and are suitable for the respective use as drug, animal feed, food supplement or food additive, or can determine them by simple tests known in the prior art.

"Dietary additives" are taken to mean additives necessitated by use of the inventive preparation as a dietary composition or as diet-supporting preparation. Dietary additives can also act as substitutes for substances which are unwanted in a diet. Such dietary additives assist, for example, in preparations which are reduced in calories. Examples of dietary additives are, for example, vitamins, minerals, trace elements or electrolytes. Vitamins which may be present are, for example, the vitamins A, B, D, E, K, thiamin, riboflavin, niacin, vitamin $B_6$, folic acid, vitamin $B_{12}$, biotin, pantheonic acid, vitamin C, choline. Minerals are, for example, calcium, phosphorus, magnesium. Trace elements comprise iron, iodine, zinc, fluorine, copper, manganese, selenium, chromium, molybdenum. Electrolytes are, for example, potassium, sodium, chlorine. Other substances which can be present are amino acids, in particular essential amino acids. Preferably, preparations which comprise dietary additives, termed below "dietary compositions", are low in fat with respect to saturated fatty acids and reduced in cholesterol. Dietary compositions can also comprise ingredients, for example fat substitutes, such as sucrose polyester (Olestra), fat replacers, for example carbohydrates, and proteins with low calories, for example protein concentrates based on casarin, soybean proteins, or hydrolysis products from starch, for example maltodextrins, or cellulose gels, or sugar replacers, for example sugar alcohols. Dietary compositions can also comprise one or more additives which support the respective diet, for example appetite-depressants or substances promoting digestion or intensive sweeteners. Intensive sweeteners are, for example, acesulfame, aspartame, saccharin, thaumatin, cyclamate. Substances promoting digestion are, for example, digestive enzymes (pancreatin), dietary fibers. Appetite-depressants are, for example, Sibutramin or Xenical.

"Additives" are also taken to mean antioxidants. Antioxidants are advantageous, for example, to protect double bonds of fatty acids against oxidation. However, the general health-promoting action of antioxidants is also known. Thus, in animal nutrition, ethoxyquin is used as antioxidant; otherwise gamma- and alpha-tocopherols, tocotrienol, rosemary extract, naturally occurring polyphenols for example flavonoids, isoflavones and carotenoids are also used.

In a further embodiment, said preparation comprises other polyunsaturated fatty acids (PUFAs). A "fatty acid" is taken to mean an unbranched carboxylic acid having an even number, from 16 to 22, of carbon atoms. "Unsaturated fatty acid" according to the invention is taken to mean a fatty acid having at least two double bonds. "Conjugated unsaturated fatty acid" is taken to mean an unsaturated fatty acid having at least two double bonds which are conjugated with respect to one another. Preferably, the preparation comprises omega-3 fatty acids, for example alpha-linolenic acid, docosatrienoic acid, docosahexanoic acid, docosapentanoic acid and/or eicosapentanoic acid, dimorphecolic acid, parinaric acid, and/or conjugated linolenic acid. The content of unsaturated fatty acids in the oil containing said octadecatrienoic acid, in particular calendic acid is preferably 30%, more preferably 40%, still more preferably 50%, 60%, 70%, 80% or 90%. Most preference is given to a content of 95%, 96%, 97%, 98%, 99% or more.

In a particularly preferred embodiment, the preparation comprises conjugated linoleic acid (CLA). As a result of the combination with CLA, the observed reduction in food intake and/or improved food utilization could be increased. Said combinations can advantageously be used in the production of drugs for treating cancer, allergies, diabetes and/or cardiovascular disorders, for example arteriosclerosis.

The inventive preparation can be solid, preferably for example freely soluble in water or oils, or liquid. The preparation, depending on the use, has the appropriate dosage form, for example for animal nutrition, as food additive or as drug. Such dosage forms are, for example, tablets, capsules, powder, granules, dragees, solutions, nutrient-defined/balanced diets, such as enteral formula and preparations for infant nutrition, fat emulsions for parenteral nutrition etc. Advantageous dosage forms of the preparations for the respective application are known to those skilled in the art. Fatty acids, in particular the inventive conjugated trans/cis octadecatrienoic acid, preferably calendic acid, can be in free form, as nontoxic salts, in particular alkali metal salt or esterified. They are preferred as ethyl or methyl esters, glycerides, or as, in particular, triglycerides or phospholipids. Preferred triglycerides are structured triglycerides in which the positional isomers are specified, particularly preferably when the conjugated trans/cis octatrienoic acid is at S2 and other short-chain fatty acids are at S1 and S3. The term glycerides comprises mono-, di- and triglycerides, preferably containing $C_1$ to $C_{22}$ fatty acids.

Flavorings can also be added to said preparations.

In foods, the preparation can be combined with customary food components. These include plant products, but also animal products, in particular sugars, if appropriate in the form of syrups, fruit preparations such as fruit juices, nectar, fruit pulps, purees or dried fruits; cereal products and starches of said cereals; milk products, such as milk protein, whey, yogurt, lecithin and lactose. Further additives are described, for example, in Park, Lipids, 32, 1997, p. 853.

In one embodiment, the inventive preparation is suitable for use in animal nutrition and comprises, for example, feed additives. "Feed additives" are taken to mean substances which serve for improving product properties, such as dust behavior, flow properties, water absorption capacity and storage stability. Examples of such feed additives and/or mixtures thereof can be those based on sugars, for example lactose or maltodextrin, based on cereal or legume products, for example corn cob grits, wheat bran and soybean meal, based on mineral salts, inter alia calcium salts, magnesium salts, sodium salts, potassium salts, and also D-pantothenic acid or its salts themselves (salt of D-pantothenic acid prepared chemically or by fermentation).

The present invention further relates to preparations which comprise inactive, viable and/or growing contents of organisms producing said octadecatrienoic acid, in particular calendic acid, or other additives. Preferably these are microorganisms, preferably fungi, yeasts and/or bacteria. Particularly preferably, the inventive animal feed comprises inactive, viable and/or growing contents of fungi of the genus *Mucor*, yeasts of the genus *Saccharomyces* and/or bacteria of the *Enterobacteriaceae*, such as *E. coli, Salmonellae*, such as *Salmonella typhimurium, Proteus vulgaris*, Pseudomonads, such as *Pseudomonas matophilal*, Bacillaceae, such as *Bacillus subtilis* or *Bacillus cereus*, coryneform bacteria, such as *Corynebacterium glutamicum* or *Brevibacterium breve* and/or *Actinum mycetalis* and/or mixtures thereof. Very particular preference is given to bacteria of the genus *Bacillus* and, in this case, of the species *Bacillus subtilis*. Also, genetically modified and/or transgenic organisms and/or production strains suitable for producing the inventive preparation are included in the invention. The enumeration above is not limiting here for the present invention.

If conjugated trans/cis-octadecatrienoic acids, in particular calendic acid, are administered individually or in combination in feed, the active compounds are administered as pure substance or mixtures of substances or liquid or solid extracts together with customary feed constituents. Examples of customary feed constituents are: corn, barley, wheat, oats, rye, triticale, sorghum, rice and brans, semolina brans and flours of these cereals, soybeans, soybean products such as soybean extraction meal, rapeseed, rapeseed extraction meal, cotton seed and extraction meal, sunflower seed, sunflower seed extraction meal, linseed, linseed extraction meal, oilseed expeller cakes, field beans, peas, gluten, gelatin, tapioca, yeasts, single cell proteins, fishmeal, salts, minerals, trace elements, vitamins, amino acids, oils/fats and the like. Advantageous compositions are described, for example, in Jeroch, H. et al. Ernährung landwirtschaftlicher Nutztiere (Farm animal nutrition), UTB.

Further suitable additives are described in Park, Lipids, 32, 1997, p. 853.

The inventive preparation can exist as powder, granules, pellets, coated extrudates and/or combinations thereof. The preparation of the inventive animal feed, for example by means of coating compounds, serves, for example, to improve product properties, such as dust behavior, flow properties, water absorption capacity and storage stability. Such preparations are widely known in the prior art. Thus, in animal nutrition, for example, blocks of a solid, cohesive shape-retaining mix of several kilos are used.

Animal diets are composed in such a manner as to cover optimally the nutrient requirements for the respective animal species. Generally, the sources of crude protein selected are plant feed components such as cornmeal, wheatmeal or barleymeal, soybean wholemeal, soybean extraction meal, linseed extraction meal, rapeseed extraction meal, green flour or ground peas. To ensure an appropriate energy content of the feed, soybean oil or other animal or vegetable fats are added. Since the plant protein sources contain only inadequate amounts of some essential amino acids, feeds are frequently enriched with amino acids. These are primarily lysine and methionine. To ensure that the farm animals are supplied with minerals and vitamins, these are also added. The type and amount of added minerals and vitamins depends on the animal species and is known to those Skilled in the art (see, for example, Jeroch et al., Ernährung landwirtschaftlicher Nutztiere, Ulmer, UTB). To cover the nutrient and energy requirements, complete feeds can be used which comprise all nutrients in a ratio to one another covering requirements. This forms the sole feed of the animals. Alternatively, a supplementary feed can be added to a cereal grain feed. The supplementary feeds are protein-, mineral- and vitamin-rich feed mixtures that usefully supplement the grain feed. It is also advantageous, in particular, for animal nutrition, that feed utilization can be improved by the present invention. The present invention can thus be used for improved animal nutrition, as described in the examples or in the prior art for CLA, and save high costs.

In addition, the invention relates to an inventive preparation that is a drug.

Improved food conversion, as has been observed for calendic acid, can lead to shorter convalescence, for example, in the case of persons or animals weakened by illness. Also, the inventive preparation can be used for changing body composition. In particular, reduced fat content can be achieved. In addition, there is a need for preparations which prevent a loss of body protein, as occurs, for example, when increased amounts of cytokinins are excreted in the body, for example TNF.

It is thought that calendic acid, surprisingly, has similar properties to CLA. The drug produced using the inventive preparation can therefore also be used for treating cancer, cardiovascular disorders, for example atherosclerosis (MacDonald, J. J. American College of Nutrition, (2000) 19, 111S-118S), diabetes (WO 99/29317), allergies, and for diets accompanying disorders.

Thus, for example, the use of said preparation is advantageous for accelerated build-up of the body, for example after relatively long illness accompanied by loss of weight, for example chemotherapy, either to support or accelerate the convalescence process.

The drug, in addition, can comprise other active compounds, for example the abovementioned or other compounds. The active compounds can be used for treating cancer, cardiovascular disorders, for example arteriosclerosis, diabetes, allergies and to support diets, or to enhance the action of the inventive preparation. A drug for treating diabetes can comprise, for example, insulin, sulfonylureas, sulfonamides, lipoic acid, γ-glucosidase inhibitors, thiazolidinediones, metformin and/or acetylsalicylic acid. Cancers are treated, for example, by adding cytostatics, such as vinca alkaloids, alkylating agents, for example chlorambucil, melphalan, thio-TEPA, cyclophosphamide, etc., by folic acid analogs, such as aminopterin or methotrexate, or by adding immunosuppressives, for example cyclophophosphamide and azathioprine, glucocorticoids, such as prednisolone, or cyclosporin. HIV infections or AIDS can be treated, for example, by administering reverse transcriptase inhibitors and/or protease inhibitors. Allergies are treated, for example, by stabilizing the mast cells, for example using cromoglyxate, by blockading the histamine receptors, for example by H1-antihistamines, or by functional antagonists of the allergy mediators, for example by alpha-sympathomimetics, adrenalin, beta2-sympathomimetics, theophylline, ipratropium or glucocorticoids. Cardiovascular disorders are treated using coagulation inhibitors, ACE inhibitors, cholesterol-lowering agents such as statins and fibrates, niacin and cholystyramine.

The drug can comprise a pharmaceutically compatible carrier. Examples of suitable pharmaceutically compatible carriers are known in the prior art and include physiologically harmless salts, for example phosphate-buffered salines, water, emulsions, for example oil/water emulsions, sterile solutions etc. Sterile solutions can be, for example, aqueous or non-aqueous solutions. Aqueous solutions are, for example, water, alcohol/water solutions, emulsions or suspensions and include sodium chloride solutions, Ringer's dextrose, dextrose and sodium chloride etc. Examples of non-aqueous solutions are propylenes, glycol, polyethylene glycol, vegetable oils, organic esters, for example ethyl oleate. In addition, the drug can comprise one of the abovementioned suitable additives. Drugs can be administered in a conventional manner orally or parenterally (subcutaneously, intravenously, intramuscularly, intraperitoneally). They can also be administered via the nasal/throat cavity using vapors or sprays.

The dosage depends on age, condition and weight of the patient and on the type of application. Generally, the daily dosage of active compound is from about 0.05 to 100 mg/kg of bodyweight for oral administration and from about 0.01 to 20 mg/kg of bodyweight for parenteral administration. Particular preference is given to from 0.5 to 50 mg/kg.

The novel compounds can be used in the solid or liquid state in the conventional pharmaceutical dosage forms, for example as tablets, film tablets, capsules, powders, granules, dragees, suppositories, solutions, lotions, creams or sprays. Sterile water may be added to solutions or suspensions for parenteral injection. These said forms are manufactured in a conventional manner. The active compounds in this case can be processed together with the customary pharmaceutical aids, such as tablet binders, fillers, preservatives, tablet disintegrators, viscosity controlling agents, emollients, wetting agents, dispersants, emulsifiers, solvents, retarding agents, antioxidants and/or propellant gases (see H. Sucker et al.: Pharmazeutische Technologie [Pharmaceutical technology], Thieme-Verlag, Stuttgart, 1991). The resultant dosage forms comprise active compounds including calendic acid or calendula oil, usually in an amount from 0.1 to 90% by weight.

An inventive preparation, in particular an inventive drug or dietary composition, can be manufactured, for example, by producing crude extracts from plants or microorganisms which comprise calendic acid, and formulating them. Standard manufacturing processes for drugs or dietary compositions are sufficiently known to those skilled in the art.

In a further embodiment, the inventive preparation can be a dietary composition; use of the dietary composition for reducing the fat content of humans or animals is advantageous. A dietary composition can comprise the abovementioned dietary additives or else other nutrients or additives. Suitable additives are, for example, dietary fiber, chitosan, carnitine, choline, caffeine or amino acids, for example essential amino acids or, for example, tyrosine, valine, leucine, threonine, tryptophan, methionine, arginine, histidine or glutamine.

Depending on the purpose, the amount of conjugated trans/cis-octadecatrienoic acid used, for example, calendic acid, must be adapted. The amount of calendic acid used can be, for example, 0.01% or 0.1% of the amount of fat added in the diet. Also, preference is given to 0.5%, 1%, 2% or 3%, 5% or 10% calendic acid. This can also apply to other fatty acids.

Furthermore, the inventive preparation can be used for reducing food intake, changing the body composition, and for improving food utilization in humans or animals. In particular, the inventive preparation can be used for reducing the fat content in relation to the body protein content.

In animals, in particular during fattening, improved food utilization is advantageous. Even a small reduction in food intake can lead to a significant decrease in feed costs. Preferably, feed consumption can be decreased by 1% or 2%, still more preferably 3%, still more preferably 5%, 10% or more.

For reducing the fat content, the content of fats supplied is replaced by the conjugated trans/cis-octadecatrienoic acid. Preferably, the content of conjugated trans/cis-octadecatrienoic acid of the fat supplied is at least from 0.1 to 50% by weight, preferably from 0.5 to 30% by weight, more preferably from 1 to 20% by weight, based on an energy intake consisting of 30% of fat, that is to say from approximately 70 to 90 g of fat/day (as in: Referenzwerte für die Nährstoffzufuhr [Reference Values for Nutrient Supply], 2000, Deutsche Gesellschaft fur Ernährung, Umschau Braus GmbH Verlagsgesellschaft).

In a further embodiment, the present invention relates to a process for adding the inventive preparation to the diet, which comprises adding conjugated trans/cis-octadecatrienoic acid, in particular calendic acid, to the fat carrier of the diet.

Various manufacturing processes are known to those skilled in the art for producing the inventive preparation. The starting material used can be, for example, plant material. Calendula oil can be obtained, for example, from the seed of *Calendula officinalis* (marigolds). Table 2 shows that the fatty acid pattern of different calendula oils from marigold seeds varies depending on their type of manufacture. Such a variation is considered to be included by the present preparation. Calendula oil can be obtained from plant seeds by pressing, for example, seeds having a high husk content, or dehusked seeds. The presscakes can also be pressed repeatedly. Plant seeds or other plant parts, for example leaves, tubers, stems, blossoms, fruits, etc. can be used from any plant which contains calendic acid. Whole plants can also be used. It is known that *Calendula officinalis* has a high calendic acid content and is therefore particularly suitable for producing calendula oil. Calendic acid and thus also also calendula oil can also be produced synthetically, however (U.S. Pat. No. 3,356,694).

Calendic acid can also be prepared by selective introduction of double bonds by Wittig reaction or metathesis. Alternatively, calendic acid can be prepared from oils containing octadecatrienoic acid. These octadecatrienoic acids can be conjugated using propylene glycol at 150° C.

Calendic acid or its esters can be prepared by isomerization at the double bond of an octadecatrienoic acid in the presence of $NaHSO_4$ or $KHSO_4$. This reaction can be carried out for dehydrated castor oil.

Calendic acid can be prepared in a similar manner to the preparation process for CLA from oils containing octadecatrienoic acid: for example, in one process the isomerization of linoleic-acid-containing oils is carried out using KOH in propylene glycol at 150° C. Free CLA acids are obtained which have only low contents of unwanted isomers (EP-839897). In an advantageous process, alkyl esters of linoleic acid can be isomerized using catalytic amounts (from 0.3 to 1%) of base (potassium alkoxide), in which case CLA alkyl esters in high purity are obtained (DE-1156788 and DE-1156789). Conjugated fatty acids and their esters can be isomerized at the double bond, for example, in the presence of $NaHSO_4$ or $KHSO_4$, see also DE-1141690.

It is also advantageous that much conjugated trans/cis-octadecatrienoic acid, in particular calendic acid, is synthesized in plants in contrast to CLA. Plants may be cultivated simply and in large amounts and therefore are an inexpensive resource for the production of, for example, calendula oil or calendic acid. In particular, plant species which are of great importance for nutrition and feeding can be transformed, for example various cereal species, potatoes, rice, corn etc., so that they synthesize calendic acid, for example. This would have the advantage that comprehensive supply of the population can be achieved simply with the basic foodstuffs. On the other hand, special oil-producing plant species, for example rapeseed, soybean, borage, olives, linseed, sunflowers etc. can be transformed in order to produce large amounts of calendula oil or to isolate calendic acid therefrom.

Microorganisms are also suitable for producing conjugated trans/cis-octadecatrienoic acids, in particular calendic acid, such as thraustochytrium or schizochytrium strains, algae such as *Phaeodactylum tricornutum* or *Crypthecodinium* species, ciliates such as *Stylonychia* or *Colpidium*, fungi such as *Mortierella, Entomorphthora* or Mucor. By strain selection, a number of mutant strains of the corresponding microorganisms have been developed that produce a number of desirable compounds, including PUFAs, and which are also suitable for producing said fatty acids or oils. In particular, microorganisms can be produced by suitable transformations, for example using nucleic acid molecules coding for desaturases or elongases.

The calendula oil or the calendic acid, the other PUFAs, and/or the additives, for example vitamins etc., which are present in the inventive preparation can either be prepared synthetically or isolated as described above from organisms, in particular microorganisms and plants. To isolate the calendic acid, the other PUFAs and a number of other said components, for example vitamins, particularly transgenic microorganisms or plants are suitable which have been transformed in such a manner that they overexpress/over-synthesize one or more of said components. For example, said components may be isolated from other eukaryotic organisms such as plants, such as *Calendula stellata, Osteospermum spinescens* or *Osteospermum hyoseroides*, algae, dinoflagellates or fungi. The inventive preparation can cover both crude extracts from organisms which synthesize the components, and other preparative treatments of these extracts, for example dryings., distillations, fractionations etc. A crude extract is a minimum preparative treatment of the sources, for example drying leaves of a plant synthesizing calendic acid, pelleting synthesizing microorganisms from a culture, etc. Plants and plant parts (seeds, leaves, etc.), can also be added to the diet directly or in concentrated form (silage, hay).

It is particularly advantageous if the inventive conjugated cis/trans-octadecatrienoic acid produced in plants or microorganisms does not need to be worked up, for example by production in plants which serve directly for food intake, or by microorganisms which are used in fermentation processes, for example in the production of cheese, yogurt, beer. Therefore, the present invention also relates to such plants. In particular, transgenic economic plants, for example corn, rice, cereals, potatoes or transgenic oil-producing plants which produce calendic acid, for example linseed, sunflowers, olives or plants whose natural calendic acid content has been increased by classic or transgenic breeding.

In a further embodiment, the present invention also relates to a kit comprising the inventive preparation. The preparation can be packaged in one or more containers. The constituents of the inventive preparation, in particular calendula oil or calendic acid can be packaged separately or together in a container of the kit. The kit can be used for carrying out the inventive process and can comprise instructions for carrying it out.

Various documents are cited in the present text of this description. Each of the documents (including manufacturers' instructions and descriptions) is hereby incorporated by reference into the description. However, this does not mean that any of said documents is actually prior art for the present invention.

The present invention will be explained by the examples and drawings below, without these being considered to be limiting in any manner.

EXAMPLES

Animals, Diets and Analyses of Body Composition 6-week-old male and female ICR mice were obtained from Charles River. 24 animals (12 m/f were randomly assigned to each experimental group. Animals were raised in groups of 4 animals at 25° C. and 60% relative humidity. A semisynthetic feed, as described in Park, Lipids, 1997: 32, 853-858, was prepared and comprised the following components:

sucrose, casein, corn starch, 5.5% corn oil, mineral and vitamin mix and ethoxyquin (100 ppm). In the experimental feed, the corn oil was replaced by an appropriate amount of crude calendula oil (BiRo, Sonunerschenburg, Germany).

TABLE 1

| Experimental group | |
|---|---|
| Experiment | Calendula oil [%] |
| 1 | — |
| 2 | 0.5 |
| 3 | 1.0 |
| 4 | 2.0 |

The calendula oil used contained approximately 62% calendic acid (as triglyceride). The fatty acid composition of the calendula oil is given in Table 2.

TABLE 2

| Fatty acid composition of the calendula oil | |
|---|---|
| Fatty acid | [%] |
| C16:0 | 2.3 |
| C18:2 (c9, 12) | 26.4 |
| C18:3 (t8, t10, c12) | 62.7 |
| Others | 5.6 |
| Total | 97.0 |

After a one-week adaptation period using control feed, a four-week experiment was carried out. Bodyweight and feed intake were measured weekly. At the end of the study the animals were killed and viscera and organs such as liver, heart and lungs were removed. The empty carcasses were frozen in liquid nitrogen, homogenized and dry weight, protein, fat and ash were determined by standard methods (LUFA Speyer).

Figure 1:
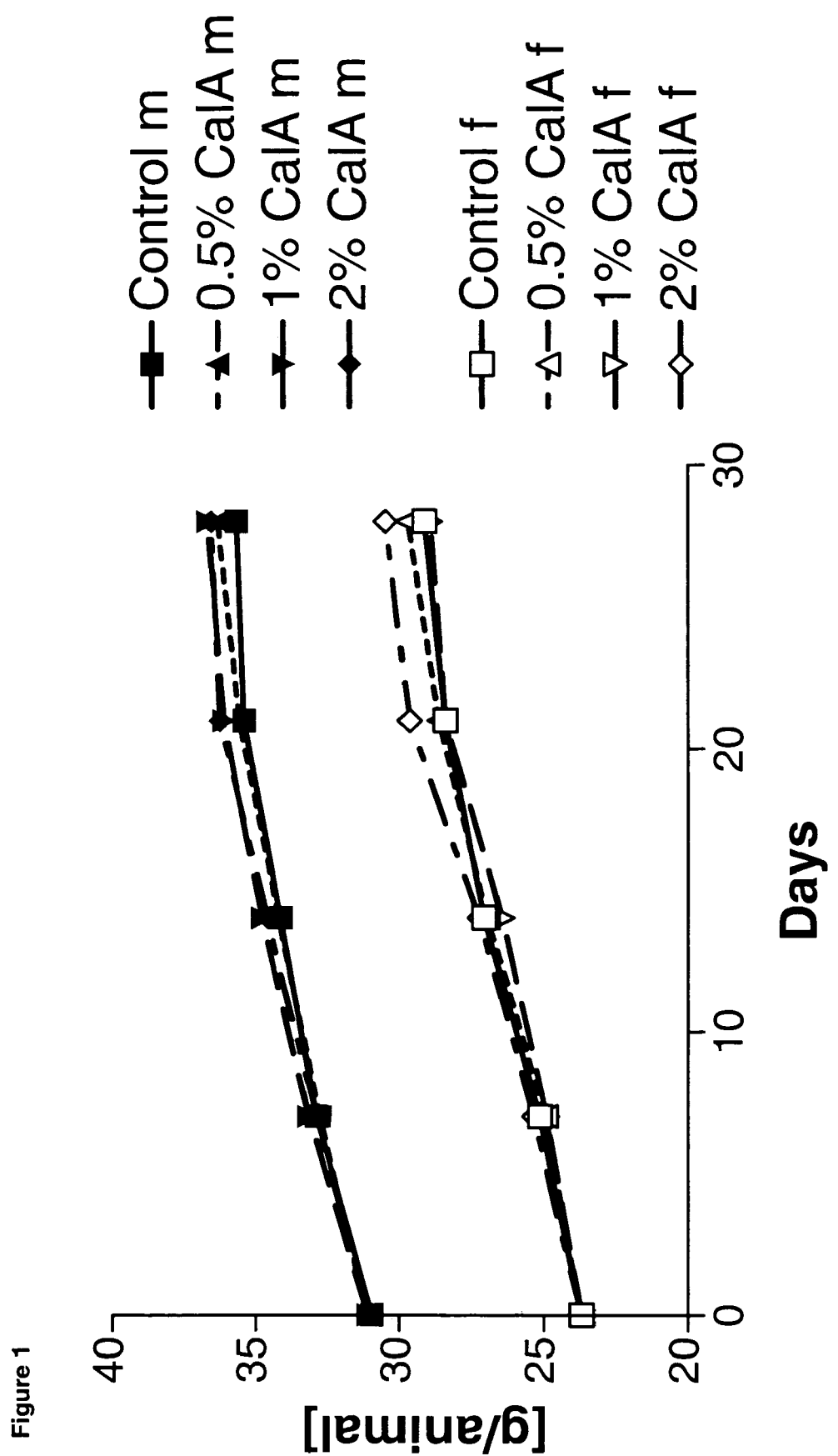
FIG. 1 describes the changes in bodyweight after calendic acid treatment.
Figure 2:
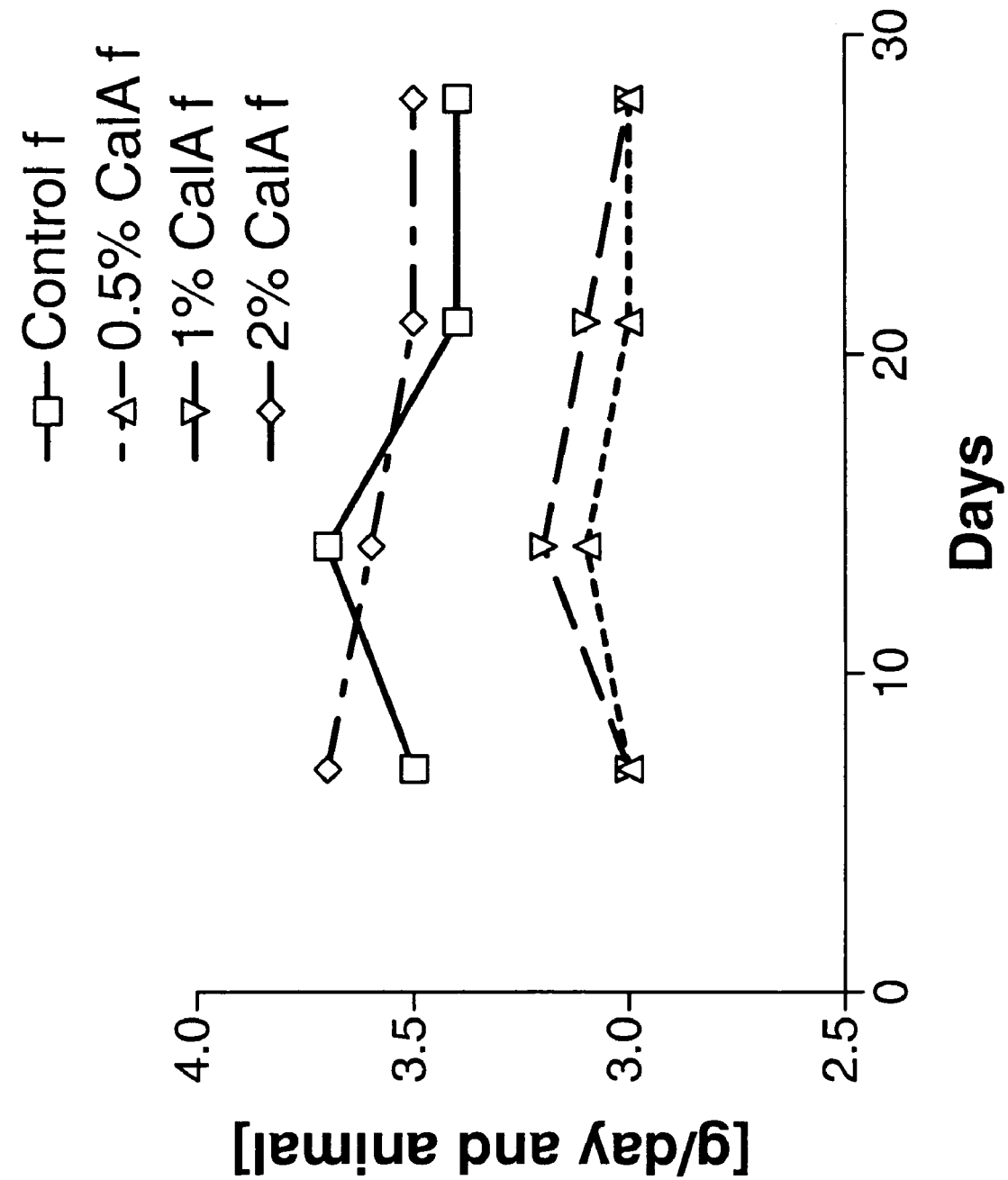
FIG. 2 describes feed intake of female and male mice after calendic acid treatment.
Figure 3:
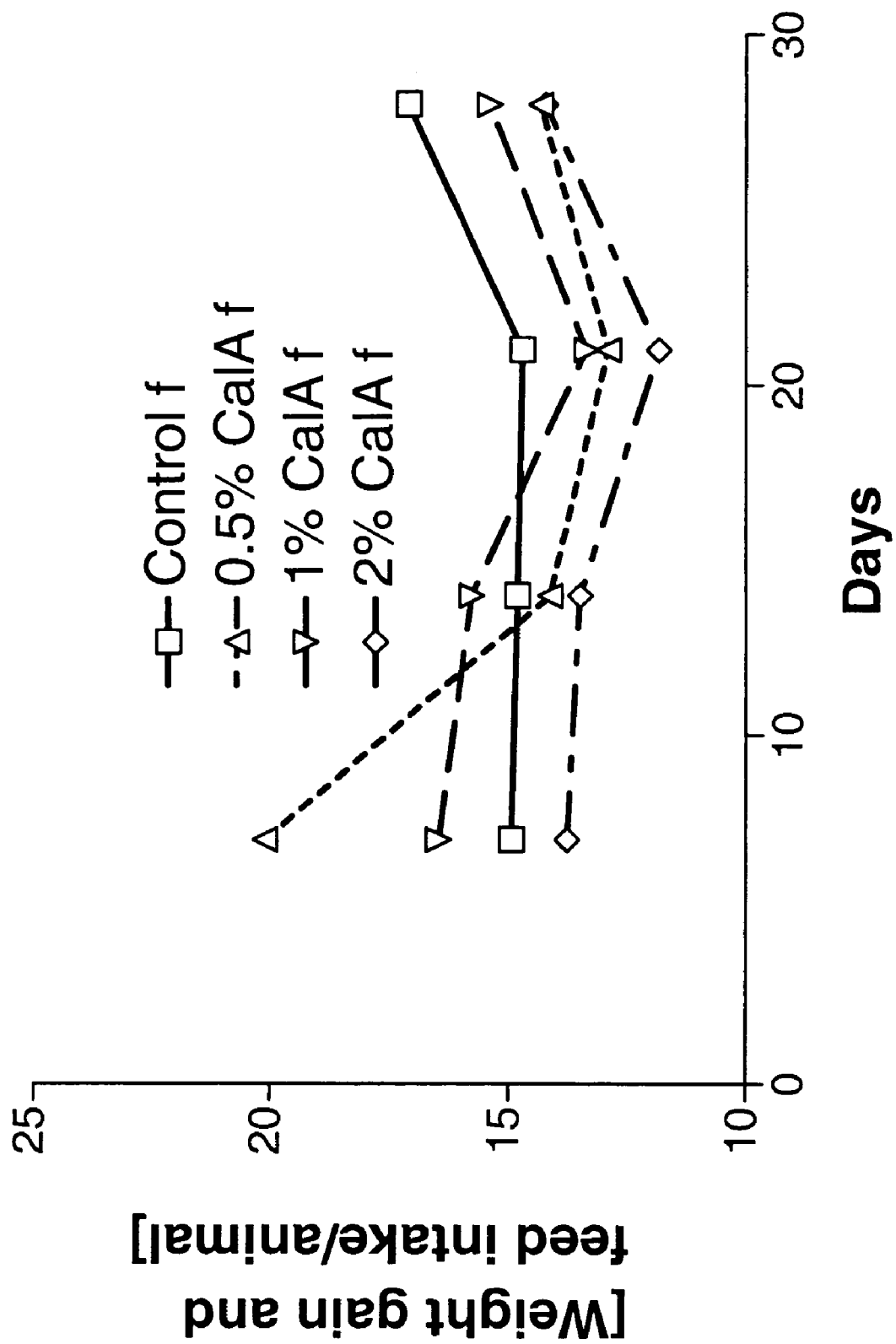
FIG. 3 describes feed utilization of female and male mice after calendic acid treatment.
Figure 4:
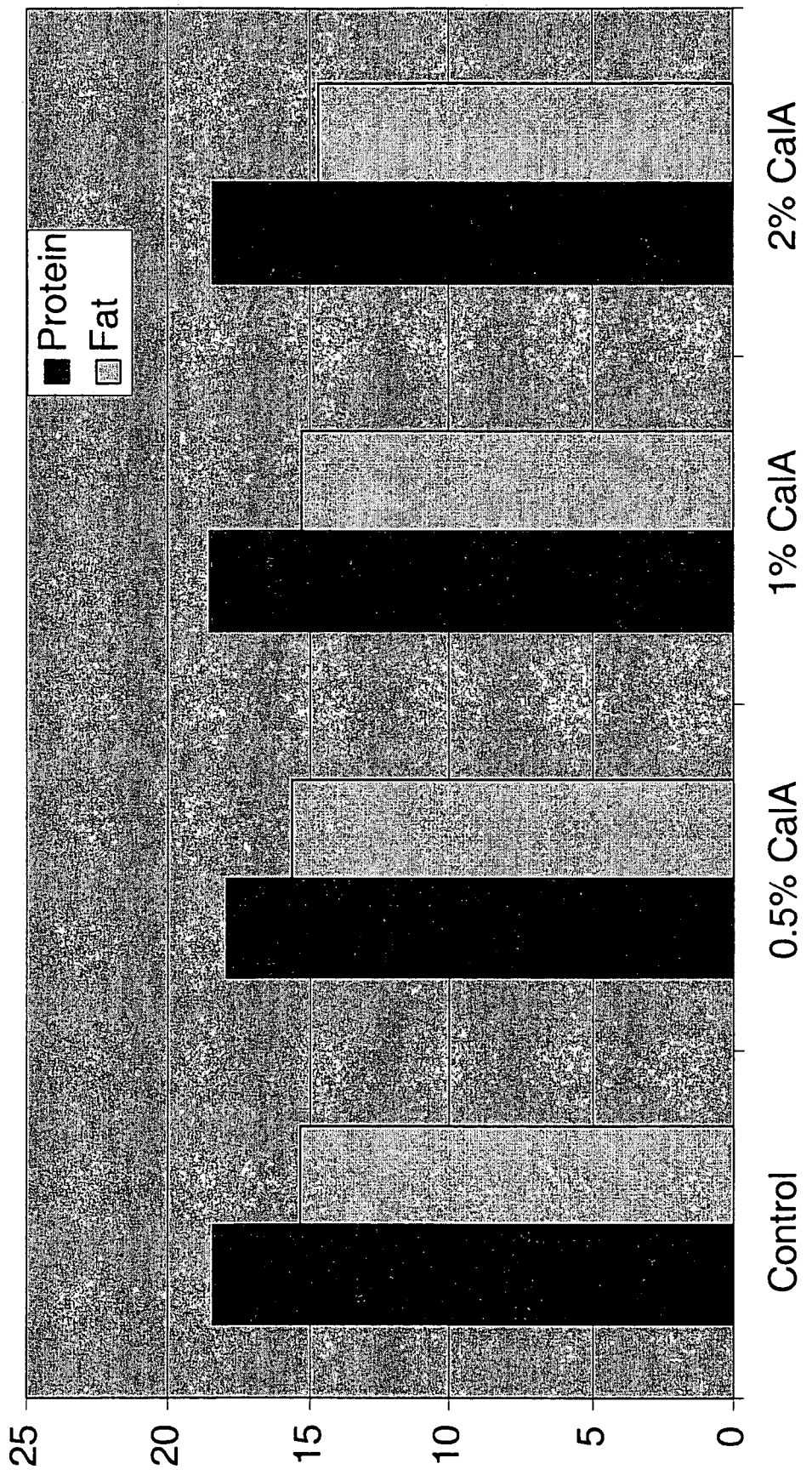
FIG. 4 describes the body fat and protein composition of female mice after calendic acid treatment.

Bodyweight, feed intake and feed utilization were calculated for a group of 4 animals and the results were shown as means. The use of calendic acid in the feed led to a reduced feed intake in the mice studied (FIG. 2), without affecting weight gain (FIG. 1). A dose-dependent effect towards reduced feed intake was observed in the male animals. Feed utilization was significantly improved in the male animals, again in a dose-dependent manner (FIG. 3). A similar trend was observed in the female animals (FIG. 3). The observed reduction in feed intake was the result of improved feed utilization after calendic acid administration (FIG. 4). The animals were able to maintain their normal weight gain (FIG. 3).

Example 2

Effects of Calendic Acid on Body Composition 5-6-week-old male and female ICR mice were obtained from Charles River. 18 animals (9 m/f) were randomly assigned to each experimental group. The animals were raised in groups of 3 animals at 20° C. in a 12-hour light/dark cycle. A semisynthetic feed, as described in Park, Lipids, 1997: 32: 853-858, was prepared. It comprised the following components: sucrose, casein, corn starch, DL-methionin, 5.5% of a mixture of vegetable oils (so that the feed comprised 0.6% linolenic acid and 3% linoleic acid of the total lipids), mineral and vitamin mix and Ethoxyquin (0.1 g/kg). In the experimental feed, the amount of vegetable oils was replaced by the corresponding amount of calendic acid. Calendic acid was present here as the ethyl ester and was obtained from calendula oil (BiRo, Sommerschenburg, Germany).

TABLE 1

| Experimental groups | |
|---|---|
| Group | Calendic acid [%] |
| 1 | Control |
| 2 | 1.0 |

After a one-week adaptation period on control feed, a six-week experiment was carried out. Body weight and feed intake were measured weekly. At the end of the study the animals were killed and viscera and organs such as liver, heart and lungs were removed. The empty carcasses were frozen in liquid nitrogen, homogenized, and the contents of fat, protein and ash were determined by standard methods.

Results:

The changes in body weight of the two groups were comparable. However, there were marked differences in the body composition of the animals, especially concerning body fat content.

Calendic acid significantly decreased the fat content in the experimental animals. The effect was greater in male animals than in female animals:

TABLE 2

Body fat content (in % of body composition)

| Group | Male animals | Female animals |
|---|---|---|
| Control | 12.2% fat | 10.3% fat |
| Calendic acid | 8.0% fat | 9.5% fat |

We claim:

1. A food preparation, food supplement preparation, or animal feedstuff preparation comprising a fatty acid mixture which has a content of calendic acid of at least 30% wherein the fatty acid mixture further comprises lipoic acid, conjugated linoleic acid (CLA) and/or carnitine.

2. The preparation defined in claim 1, which comprises calendic acid in form of calendula oil.

3. A food preparation, food supplement preparation, or animal feedstuff preparation comprising a fatty acid mixture which has a content of calendic acid of at least 30%, wherein the fatty acid mixture further comprises one or more polyunsaturated fatty acids (PUFAs).

4. The preparation defined in claim 3, wherein the one or more polyunsaturated fatty acids comprise conjugated linoleic acid.

5. The preparation defined in claim 1, further comprising one or more additives.

6. The animal feedstuff preparation defined in claim 1, further comprising one or more additives.

7. A process for reducing food intake and/or for improving food utilization and/or for reducing the percentage of body fat in a human or an animal, which process comprises administering to the human or to the animal an effective amount of a food preparation, food supplement preparation or animal feedstuff preparation comprising a fatty acid mixture which has a content of calendic acid of at least 30%.

8. A process for reducing food intake and/or for improving food utilization and/or for reducing the percentage of body fat in a human or an animal, which process comprises administering to said human or animal an effective amount of calendula oil or calendic acid in form of a drug preparation comprising, in addition to a pharmaceutically compatible carrier, from 0.1 to 90% by weight of calendic acid or calendula oil.

9. A process as claimed in claim 8, wherein the drug preparation is administered such that calendic acid is administered orally in a daily dosage of from about 0.05 to 100 mg/kg of bodyweight, or such that calendic acid is administered parenterally in a daily dosage of 0.01 to 20 mg/kg of bodyweight.

* * * * *